United States Patent [19]

Dellinger et al.

[11] Patent Number: 5,376,613
[45] Date of Patent: Dec. 27, 1994

[54] DEHYDROGENATION CATALYST AND PROCESS FOR PREPARING SAME

[75] Inventors: Philip W. Dellinger; Rebecca G. Moore; Fred A. Sherrod; Allen R. Smith, all of Lake Jackson, Tex.

[73] Assignee: The Dow Chemical Company, Midland, Mich.

[21] Appl. No.: 58,192

[22] Filed: May 4, 1993

[51] Int. Cl.$^5$ .............. B01J 23/78; B01J 23/02; B01J 23/04; B01J 27/055

[52] U.S. Cl. .................. 502/304; 502/218; 502/241; 502/243; 502/439

[58] Field of Search .............. 502/304, 306, 324, 328, 502/439, 218, 243, 241

[56] References Cited

U.S. PATENT DOCUMENTS

| | | |
|---|---|---|
| 2,990,432 | 6/1961 | Fleming et al. ............... 502/243 X |
| 3,361,683 | 1/1968 | Gutmann ...................... 502/312 X |
| 3,448,058 | 6/1969 | Arnold ......................... 502/329 X |
| 3,703,593 | 11/1972 | Turley et al. .................. 502/316 |
| 3,904,552 | 9/1975 | O'Hara ......................... 502/304 X |
| 4,467,046 | 8/1984 | Smith et al. .................. 502/304 X |
| 4,503,163 | 3/1985 | Chu ............................. 502/306 X |
| 4,684,619 | 8/1987 | Moore .......................... 502/330 |
| 4,758,543 | 7/1988 | Sherrod et al. ................ 502/174 |
| 4,804,799 | 2/1989 | Lewis et al. ................... 502/304 X |
| 5,023,225 | 6/1991 | Williams et al. ............... 502/304 |
| 5,190,906 | 3/1993 | Murakami et al. ............. 502/304 |

Primary Examiner—Paul Lieberman
Assistant Examiner—Douglas J. McGinty

[57] ABSTRACT

A calcined dehydrogenation catalyst comprising at least one sodium compound and one calcium compound is disclosed. The catalyst exhibits improved moisture stability as evidenced by improved crush strength and resistance to swelling and cracking.

14 Claims, No Drawings

DEHYDROGENATION CATALYST AND PROCESS FOR PREPARING SAME

BACKGROUND OF THE INVENTION

This invention relates to improved catalysts for the dehydrogenation of hydrocarbons and to a method of making such catalyst compositions which exhibit improved moisture stability when subjected to contact with hydrogen and steam at elevated temperatures during the dehydrogenation process. This improved stability is evidenced by improved crush strength and resistance to swelling and cracking.

TECHNICAL BACKGROUND

Catalytic dehydrogenation of hydrocarbons using various catalyst compositions has been known from just prior to World War II. Commercial examples are the manufacture of styrene and butadiene from ethylbenzene and butylene. Promoted iron oxide catalysts have been found to be especially useful in the dehydrogenation of alkyl aromatic hydrocarbons to vinyl aromatic hydrocarbons. Most commercial iron oxide dehydrogenation catalysts include minor amounts of promoters, e.g., salts or oxides of chromium, manganese, bismuth, tungsten, or molybdenum, with chromium being preferred, together with a compound of potassium, e.g., potassium oxide or carbonate. The potassium compound gives the catalyst a self-regenerative property that prolongs its useful life for long periods of time without significant loss of activity. Recent improvements include the incorporation of minor amounts of vanadium and modifiers, such as carbon black or graphite and methyl cellulose, which can beneficially affect the pore structures of the catalysts.

The catalyst life of dehydrogenation catalysts is often dictated by the pressure drop across a reactor. An increase in the pressure drop lowers both the yield and conversion to the desired product. Physical degradation of the catalyst typically increases the pressure drop across the reactor. For this reason, the physical integrity of the catalyst is of major importance. Dehydrogenation catalysts containing iron oxide can undergo substantial changes under process conditions which decrease their physical integrity. For example, in the dehydrogenation of ethylbenzene to styrene, the catalyst is subjected to contact with hydrogen and steam at high temperatures and, under these conditions, $Fe_2O_3$, the preferred source of iron for the production of styrene catalysts, is reduced to $Fe_3O_4$. This reduction causes a transformation in the lattice structure of the iron oxide, resulting in catalyst bodies which have poorer physical integrity and are very susceptible to degradation by contact with water at temperatures below 100° C. This degradation by contact with water is characterized by the catalyst bodies (e.g., pellets or granules) becoming soft and/or swollen and/or cracked. The water which contacts the catalysts may be in the form of liquid or a wet gas, such as air with a high humidity. "High humidity" refers to a relative humidity above about 50%.

The catalysts in styrene production plants are often exposed to temperatures below 100° C. during start-ups, shutdowns, and upsets. Because large amounts of steam are used in styrene production, there is significant potential for exposing the catalyst to moisture at low temperatures.

As previously discussed, this exposure causes physical degradation of the catalyst, which increases pressure drop across the reactor, resulting in decreased catalyst life.

In recent years, catalysts with higher amounts of potassium have been used: in U.S. Pat. No. 4,503,163 assigned to Mobil Oil Company, for example, catalysts are disclosed which contain 13–48% and preferably 27–41% by weight of a potassium promoter compound, calculated as potassium oxide. Such catalysts are self regenerative catalysts which perform well at lower steam to oil ratios; e.g., ratios of <2:1 (by weight). The economic advantages of using less steam are obvious. The problem with using higher concentrations of potassium is that the vulnerability of the used iron oxide catalyst to moisture increases with increasing potassium concentration.

A need exists for a dehydrogenation catalyst that has both high activity, selectivity and resistance to moisture. A way has now been discovered to enhance moisture resistance of these catalysts without any significant detrimental effects to catalyst performance.

SUMMARY OF THE INVENTION

In one embodiment the invention is a novel calcined dehydrogenation catalyst comprising (a) an iron oxide; (b) a potassium and/or cesium compound; (c) at least one sodium compound in an amount from about 0.2 to about 10 weight percent sodium, calculated as sodium oxide; and (d) at least one calcium compound in an amount from 1.5 to 20 weight percent calcium calculated as calcium oxide.

In a second embodiment, the invention is a process for preparing such improved dehydrogenation catalysts. This process comprises the steps of (a) preparing an extrudate by admixing iron oxide, a potassium and/or cesium compound, at least one sodium compound in an amount from about 0.2 to about 10 weight percent sodium calculated as the oxide, at least one calcium compound in an amount from 1.5 to 20 weight percent calcium calculated as calcium oxide and sufficient water to form an extrudable mixture; (b) forming said extrudable mixture into pellets; and (c) calcining said pellets into a finished catalyst.

The new catalyst compositions are useful for the dehydrogenation of an alkyl aromatic compound to form a vinyl aromatic compound by contacting the alkyl aromatic compound with the dehydrogenation catalyst under dehydrogenating conditions. The new catalysts have improved moisture stability, as evidenced by improved crush strength, which decreases catalyst degradation during process upsets.

DETAILED DESCRIPTION OF THE INVENTION

The invention resides in the discovery that the addition of sodium and calcium compounds to known dehydrogenation catalysts produce new dehydrogenation catalysts having improved stability. Thus, any of the known class of dehydrogenation catalyst compositions containing red or yellow iron oxides and various catalyst promoters (as disclosed, for example, in U.S. Pat. Nos. 4,503,163, 3,703,593, 4,684,619, all of which are assigned to The Dow Chemical Company, and are incorporated by reference) may be used herein. Iron is generally added to the catalyst compositions of the invention as red iron oxide, $Fe_2O_3$, or yellow iron oxide, $Fe_2O_3.H_2O$. Particularly suited are pigment grades of red and yellow iron oxides. Likewise the catalyst promoter can be any material taught by the art, for example, an alkali metal compound(s) that is converted to an alkali metal oxide under calcination conditions. Potassium compounds are the preferred promoters. The promoter can be added to the catalyst in various forms. The alkali metal oxides, hydroxides, carbonates, bicarbonates, and the like, and mixtures thereof are preferred, and potassium carbonate or a mixture of potassium carbonate with potassium oxide is most preferred.

The catalyst compositions of the present invention also may contain, and preferably do contain, cerium to enhance selectivity. Cerium, if used in the catalyst compositions of the present invention, can be added to the catalyst in the form of cerium oxide or in the form of other cerium compounds that decompose upon calcination to form cerium oxide, as for example, cerium carbonate, cerium nitrate, cerium hydroxide or any combination thereof.

Other known catalyst additives can be included in the catalysts of the invention, but are not essential. A chromium compound which can serve as a stabilizer for the active catalytic components is illustrative of an optional but preferred additive. Chromium compounds have previously been added to alkali-promoted iron oxide catalysts to extend their life. Chromium, as used in the compositions of this invention, can be added to the catalyst in the form of a chromium oxide or in the form of chromium compounds which decompose upon calcination to chromium oxides.

Another optional component, used to improve the selectivity of the catalyst, is molybdenum which can be added as its oxide or as a molybdate. Other metal compounds that may be added as promoters include compounds of aluminum, vanadium, cobalt, cadmium, copper, magnesium, manganese, and nickel, providing they can be calcined to the corresponding metal oxide.

The physical strength, activity and selectivity of the catalyst compositions of the present invention can be improved by adding certain binding agents. Binding agents can include and consist of hydraulic cements, for example, calcium aluminate or Portland cement. These cements can be added individually or in combination.

The density of the catalyst composition can be modified by the addition of various filler substances, for example, combustible materials such as graphite and methyl cellulose. Such materials can be added to the compositions during preparation, but are burned out after the catalyst pellets have been formed during the calcining step. Porosity promoting aids can also facilitate extrusion of catalyst pellets.

The catalyst components can be mixed in various ways known to the art. One method comprises ballmilling together a mixture of desired compounds, adding a small amount of water, and extruding the composite to produce small pellets, which are then dried and calcined. Another method is mixing the components together with water, drying them to form a powder and tabletizing and calcining the tablets. Another procedure involves mixing the components together with an excess of water, partially drying, and then subsequently extruding, drying, and calcining the resulting pellets. The choice of the mixing method depends on the preference of the skilled artisan.

A preferred method of preparing the catalysts is to blend the catalyst ingredients together, including the ingredients of the present invention, in the presence of sufficient water to make a moist extrudable mixture. This mixture is then extruded to produce extrudates between $\frac{1}{8}$-inch and $\frac{1}{4}$-inch in diameter. The extrudates are then calcined under conventional calcining conditions. Calcination temperatures can range from about 500° C. to about 900° C., preferably from about 600° C. to about 800° C. After calcination the extrudates are ready for use as catalysts.

The amount of sodium included in the new catalyst, measured as sodium oxide and based on the weight of the calcined catalyst may range from about 0.2% to about 10%. Preferably sodium is present in the catalyst in the range of about 0.5% to 5%. Most preferably, sodium is present in amounts of from 0.8 to 3.0%. The sodium may be added to the catalyst mixture as sodium hydroxide or carbonate or bicarbonate or other salts such as acetate, oxalate, nitrate, or sulfate.

The amount of calcium in the new catalyst, measured as calcium oxide and based on the weight of the calcined catalyst, may range from 1.5% to 20%. Preferably calcium is present in the range of about 3% to 15%. Most preferably calcium is present in amounts from 4% to 12%. Calcium can be added to the catalyst mixture in the form of calcium carbonate, calcium sulfate, calcium hydroxide, or other salts.

EXPERIMENTAL

All catalysts prepared in the following examples are prepared from commercially available chemicals. LUMNITE is the trade name for calcium aluminate cement manufactured by Lehigh Cement Company.

Examples 1-5

A catalyst formulation is made by blending in a heated steam jacketed blade mixer 135 grams(g) red iron oxide ($Fe_2O_3$), 153.4 g yellow iron oxide ($Fe_2O_3 \cdot H_2O$), 120 g calcium aluminate cement (LUMNITE), 38 g gypsum ($CaSO_4 \cdot 2H_2O$), 120 g calcium carbonate ($CaCO_3$), 10 g molybdenum oxide ($MoO_3$), 190.5 g hydrated cerium carbonate ($Ce_2(CO_3)_3 \cdot 5H_2O$), 450 g potassium carbonate ($K_2CO_3$), 10 g potassium dichromate ($K_2Cr_2O_7$), and 41.5 g of a aqueous 50% solution of sodium hydroxide (NaOH). About 15% (wt) of water is then blended into the formulation. The mixture is mixed and dried in the heated steam jacketed mixer until the formulation reaches a consistency suitable for extrusion. The hot catalyst mixture is transferred to a California Model CL-3 Laboratory Pellet Mill and extruded (5/32″ in diameter and about 10/32″ in length).

Four additional catalysts formulations are prepared according to the above procedure, but with different amounts of ingredients. Table 1 lists the formulations of Examples 1-5. The extrudates of Examples 1-5 are then calcined by slowly ramping the temperature to 775° C. over a period of about two hours, and maintaining at 775° C. for 30 minutes. The finished compositions of the calcined catalysts, expressed as shown, are given in Table 2.

TABLE 1

| Component* | Catalyst Formulation | | | | |
| --- | --- | --- | --- | --- | --- |
| | Ex. 1 | Ex. 2 | Ex. 3 | Ex. 4 | Ex. 5 |
| $Fe_2O_3$ | 135 | 135 | 135 | 135 | 135 |
| $Fe_2O_3 \cdot H_2O$ | 153.4 | 153.4 | 153.4 | 153.4 | 153.4 |
| LUMNITE | 120 | 120 | 120 | 120 | 120 |
| $MoO_3$ | 10 | 10 | 10 | 10 | 10 |
| $Ce_2(CO_3)_3 \cdot 5H_2O$ | 190.5 | 190.5 | 190.5 | 190.5 | 190.5 |
| $K_2CO_3$ | 450 | 450 | 450 | 450 | 450 |
| $K_2Cr_2O_7$ | 10 | 10 | 10 | 10 | 10 |
| $CaSO_4 \cdot 2H_2O$ | 38 | 38 | 38 | 38 | 38 |

TABLE 1-continued

| | Catalyst Formulation | | | | |
|---|---|---|---|---|---|
| Component* | Ex. 1 | Ex. 2 | Ex. 3 | Ex. 4 | Ex. 5 |
| $CaCO_3$ | 120 | 240 | 60 | 60 | 60 |
| NaOH, 50% | 41.5 | 45.8 | 19.5 | 39.3 | 66.2 |

*All weights in grams.

TABLE 2

| | Components of Calcined Catalyst | | | | |
|---|---|---|---|---|---|
| Component* | Ex. 1 | Ex. 2 | Ex. 3 | Ex. 4 | Ex. 5 |
| $Fe_2O_3$ | 23.46 | 21.21 | 25.0 | 24.78 | 24.48 |
| LUMNITE | 10.43 | 9.43 | 11.11 | 11.01 | 10.88 |
| $MoO_3$ | 0.87 | 0.79 | 0.93 | 0.92 | 0.91 |
| $Ce_2O_3$ | 10.43 | 9.43 | 11.11 | 11.01 | 10.88 |
| $K_2CO_3$ | 39.10 | 35.35 | 41.68 | 41.30 | 40.79 |
| $K_2Cr_2O_7$ | 0.87 | 0.79 | 0.93 | 0.92 | 0.91 |
| $CaSO_4$ | 2.61 | 2.36 | 2.78 | 2.75 | 2.72 |
| $CaCO_3$ | 10.43 | 18.85 | 5.56 | 5.51 | 5.44 |
| NaOH | 1.80 | 1.80 | 0.90 | 1.80 | 3.00 |

*Weight percent

COMPARATIVE EXPERIMENTS 1 to 4

The same procedure employed in Examples 1–5 was used to make all the comparative catalysts. Table 3 lists the formulations of the comparative catalysts.

TABLE 3

| | Comparative Catalyst Formulation | | | |
|---|---|---|---|---|
| Component* | Comp. Ex. 1 | Comp. Ex. 2 | Comp. Ex. 3 | Comp. Ex. 4 |
| $Fe_2O_3$ | 135 | 135 | 135 | 135 |
| $Fe_2O_3 \cdot H_2O$ | 153.4 | 153.4 | 153.4 | 153.4 |
| LUMNITE | 120 | 120 | 120 | 120 |
| $MoO_3$ | 10 | 10 | 10 | 10 |
| $Ce_2(CO_3)_3 \cdot 5H_2O$ | 190.5 | 190.5 | 190.5 | 190.5 |
| $K_2CO_3$ | 450 | 450 | 450 | 450 |
| $K_2Cr_2O_7$ | 10 | 10 | 10 | 10 |
| $CaSO_4 \cdot 2H_2O$ | 38 | 38 | — | 38 |
| $CaCO_3$ | — | 60 | — | — |
| NaOH, 50% | — | — | 36 | 39.3 |

All weights in grams.

The finished compositions of the calcined comparative catalysts, expressed as shown, are given in Table 4.

TABLE 4

| | Components of Calcined Comparative Catalysts | | | |
|---|---|---|---|---|
| Component* | Comp. Ex. 1 | Comp. Ex. 2 | Comp. Ex. 3 | Comp. Ex. 4 |
| $Fe_2O_3$ | 26.74 | 25.24 | 27.06 | 26.22 |
| LUMNITE | 11.88 | 11.21 | 12.02 | 11.65 |
| $MoO_3$ | 0.99 | 0.93 | 1.00 | 0.97 |
| $Ce_2O_3$ | 11.88 | 11.22 | 12.03 | 11.66 |
| $K_2CO_3$ | 44.55 | 42.05 | 45.09 | 43.70 |
| $K_2Cr_2O_7$ | 0.99 | 0.93 | 1.00 | 0.97 |
| $CaSO_4$ | 2.97 | 2.81 | — | 2.92 |
| $CaCO_3$ | — | 5.62 | — | — |
| NaOH | — | — | 1.80 | 1.91 |

*Weight percent

The catalysts of the invention and those prepared for comparison are tested for activity and selectivity in the reaction for dehydrogenating ethylbenzene to styrene by placing 70 or 100 milliliters (mL) of the above calcined catalyst extrudates in a fixed bed reactor and passing a preheated mixture of steam and ethylbenzene at a weight ratio of 1.5:1 (called the steam to oil ratio) through the bed which is maintained at a temperature of 580°–590° C. The LHSV (liquid hourly space velocity) is 1.0 and the pressure is maintained at atmospheric. The liquid hourly space velocity is a number denoting residence time in a reactor commonly used by those skilled in the art. After a minimum of 5 days, the weight ratio of steam to ethylbenzene is reduced to 1.2 and the bed temperature adjusted so that an ethylbenzene conversion of 50% is achieved. This temperature adjustment is continued each day until a constant conversion of about 50% is achieved at a fixed bed temperature, that temperature being an indication of the activity of the particular catalyst; i.e., the lower the temperature, the higher the activity. The results of the dehydrogenation reaction for Examples 1–5 and Comparative Experiments 1–4 are shown in Table 5.

TABLE 5

| Catalyst | Temp, °C. | Conversion | Selectivity |
|---|---|---|---|
| Example 1 | 589 | 50.0 | 97.2 |
| Example 2 | 597 | 49.8 | 97.1 |
| Example 3 | 589 | 49.7 | 96.9 |
| Example 4 | 596 | 50.3 | 96.5 |
| Example 5 | 600 | 50.5 | 97.2 |
| Comp. Ex. 1 | 598 | 50.2 | 95.9 |
| Comp. Ex. 2 | 595 | 50.4 | 96.6 |
| Comp. Ex. 3 | 590 | 50.4 | 97.1 |
| Comp. Ex. 4 | 587 | 49.7 | 96.8 |

The moisture resistance of the used catalyst is measured by the following method. After approximately two to three weeks of operation, the catalyst is unloaded from the reactor and twenty randomly chosen extrudates are placed in a glass dish with a flat bottom. The extrudates are separated so that they do not touch each other. The glass dish is then placed in a controlled relative humidity chamber (Vapor-Temp Model No. VP-100AT-1) made by Blue M, a unit of General Signal, adjusted to 30° C. and 70% relative humidity. After 20 hours the glass dish is removed from the humidity chamber. The excess water in the dish is removed, and the extrudates are placed in a drying oven at 150° C. for 24 hours. The extrudates are removed and the average crush strength of the extrudates determined.

Crush strength is a common physical measurement that indicates the strength of the catalyst body; i.e., tablet, pellet, or extrudate. In this test, catalyst bodies are compressed between two flat metal surfaces or blocks, and the pressure required to crush the body is measured. A Comten crush strength machine, model no. 922T-10-OP, serial no. 830202, is used according to the following procedure. The length of the extrudate is first measured, then the extrudate is crushed between the two blocks of the Comten unit and the pressure required to crush the extrudate is recorded. The crush strength per one-quarter inch length of extrudate is then calculated. This procedure is done on twenty randomly chosen extrudates from each catalyst sample which are all preconditioned as noted in the preceding paragraph. Averaged crush strength is expressed as "PSIG/¼ inch". The average of these twenty measurements is shown in Table 6.

TABLE 6

| Catalyst | Average Crush Strength PSIG/¼ inch. | Physical Appearance |
|---|---|---|
| Example 1 | 18.5 | Hard, No Cracking or Swelling |
| Example 2 | 18.0 | Hard, No Cracking or Swelling |
| Example 3 | 13.5 | Hard, No Cracking or Swelling |
| Example 4 | 15.5 | Hard, No Cracking or Swelling |
| Example 5 | 18.8 | Hard, No Cracking or Swelling |

TABLE 6-continued

| Catalyst | Average Crush Strength PSIG/¼ inch. | Physical Appearance |
|---|---|---|
| Comp. Ex. 1 | <5 | Soft, Cracked, Swollen |
| Comp. Ex. 2 | <5 | Soft, Cracked, Swollen |
| Comp. Ex. 3 | <5 | Soft, Cracked, Swollen |
| Comp. Ex. 4 | 6 | ½ Pellets Soft, Slightly Swollen, Other ½ Hard, No Cracking or Swelling |

We claim:

1. A calcined dehydrogenation catalyst comprising a calcination product of
   (a) at least one iron oxide;
   (b) a carbonate, bicarbonate, oxide or hydroxide of potassium or cesium, or a mixture of at least two thereof;
   (c) an oxide, carbonate, nitrate, or hydroxide of cerium, or a mixture of at least two thereof;
   (d) an hydraulic cement;
   (e) an hydroxide, carbonate, bicarbonate, acetate, oxalate, nitrate, or sulfate of sodium, in an amount sufficient to provide from about 0.8 to about 10 percent sodium, calculated as sodium oxide, by weight of the calcined catalyst; and
   (f) a carbonate, sulfate, or hydroxide, of calcium or a mixture of at least two thereof, in an amount sufficient to provide from about 4 to 20 percent calcium, calculated as calcium oxide, by weight of the calcined catalyst.

2. The calcined dehydrogenation catalyst of claim 1 wherein (e) is sodium hydroxide and (f) is calcium carbonate.

3. The calcined dehydrogenation catalyst of claim 1 containing from about 0.8 to 5 percent sodium calculated as sodium oxide and from about 3 to 15 percent calcium calculated as calcium oxide, by weight of the calcined catalyst.

4. The calcined dehydrogenation catalyst of claim 1 wherein (b) is a carbonate, bicarbonate, oxide or hydroxide of potassium, or a mixture of at least two thereof.

5. The calcined dehydrogenation catalyst of claim 4 wherein (b) is potassium carbonate or a mixture of potassium carbonate and potassium oxide.

6. The calcined dehydrogenation catalyst of claim 5 wherein
   (c) is a carbonate of cerium;
   (d) is a calcium aluminate hydraulic cement;
   (e) is sodium hydroxide, in an amount so that the catalyst contains from 0.8 to 3.0 percent by weight sodium, calculated as sodium oxide; and
   (f) is a carbonate or sulfate of calcium or a mixture thereof, in an amount so that the catalyst contains from 4 to 12 percent by weight calcium, calculated as calcium oxide.

7. The calcined dehydrogenation catalyst of claim 1 further comprising one or more oxides of chromium, molybdenum, aluminum, vanadium, cobalt, cadmium, copper, magnesium, manganese, or nickel.

8. A process for preparing a calcined dehydrogenation catalyst comprising:
   (A) preparing an extrudable mixture by admixing
      (a) at least one iron oxide;
      (b) a carbonate, bicarbonate, oxide or hydroxide of potassium or cesium, or a mixture of at least two thereof;
      (c) an oxide, carbonate, nitrate, or hydroxide of cerium, or a mixture of at least two thereof;
      (d) an hydraulic cement;
      (e) an hydroxide, carbonate, bicarbonate, acetate, oxalate, nitrate, or sulfate of sodium, in an amount sufficient to provide from about 0.8 to about 10 percent sodium, calculated as sodium oxide, by weight of the calcined catalyst; and
      (f) a carbonate, sulfate, or hydroxide, of calcium or a mixture of at least two thereof, in an amount sufficient to provide from about 4 to 20 percent calcium, calculated as calcium oxide, by weight of the calcined catalyst, with sufficient water to form an extrudable mixture;
   (B) forming the extrudable mixture into pellets; and
   (C) calcining the pellets into a finished catalyst.

9. The process of claim 8 wherein (e) is sodium hydroxide and (f) is calcium carbonate.

10. The process of claim 8 containing from about 0.8 to 5 percent sodium calculated as sodium oxide and from about 3 to 15 percent calcium calculated as calcium oxide, by weight of the calcined catalyst.

11. The process of claim 8 wherein (b) is a carbonate, bicarbonate, oxide or hydroxide of potassium, or a mixture of at least two thereof.

12. The process of claim 11 wherein (b) is potassium carbonate or a mixture of potassium carbonate and potassium oxide.

13. The process of claim 12 wherein
   (c) is a carbonate of cerium;
   (d) is a calcium aluminate hydraulic cement;
   (e) is sodium hydroxide, in an amount so that the catalyst contains from 0.8 to 3.0 percent by weight sodium, calculated as sodium oxide; and
   (f) is a carbonate or sulfate of calcium or a mixture thereof, in an amount so that the catalyst contains from 4 to 12 percent by weight calcium, calculated as calcium oxide.

14. The process of claim 8 further comprising one or more oxides of chromium, molybdenum, aluminum, vanadium, cobalt, cadmium, copper, magnesium, manganese, or nickel.

* * * * *